(12) United States Patent
Coates

(10) Patent No.: US 7,166,095 B1
(45) Date of Patent: Jan. 23, 2007

(54) PROTECTIVE UNDERGARMENTS HAVING ANCHORED POCKETED-SLING STRUCTURES AND MANUFACTURING METHODS THEREFOR

(75) Inventor: Fredrica V. Coates, Winston-Salem, NC (US)

(73) Assignee: Tailored Technologies, Inc., Winston-Salem, NC (US)

(*) Notice: Subject to any disclaimer, the term of this patent is extended or adjusted under 35 U.S.C. 154(b) by 442 days.

(21) Appl. No.: 09/791,773

(22) Filed: Feb. 26, 2001

Related U.S. Application Data

(63) Continuation-in-part of application No. 09/512,085, filed on Feb. 24, 2000, now Pat. No. 6,926,705.

(60) Provisional application No. 60/121,960, filed on Feb. 25, 1999.

(51) Int. Cl.
*A61F 13/76* (2006.01)
*A61F 13/82* (2006.01)
*A61F 13/72* (2006.01)
*A61F 13/78* (2006.01)

(52) U.S. Cl. ............ 604/385.19; 604/385.14; 604/398; 604/401

(58) Field of Classification Search ........... 604/385.01, 604/385.03, 385.14–385.15, 385.19, 385.24–385.3, 604/386–87, 391, 393–402
See application file for complete search history.

(56) References Cited

U.S. PATENT DOCUMENTS

| | | | |
|---|---|---|---|
| 2,493,492 A | * | 1/1950 | Malamut |
| 2,545,216 A | * | 3/1951 | Toussie |
| 5,137,526 A | | 8/1992 | Coates |
| 5,409,476 A | | 4/1995 | Coates |
| 5,722,127 A | | 3/1998 | Coates |

* cited by examiner

*Primary Examiner*—Karin Reichle
(74) *Attorney, Agent, or Firm*—McDermott Will & Emery LLP

(57) ABSTRACT

A protective undergarment having an outer layer of fluid-resistant material shaped to conform to the buttock and leg region of a user, and an elongated sling of material connected to the outer layer. Opposite sides of the sling are bowed inward and joined together at a first end of the sling to form a first pocket part for retaining one end of a fluid absorbent pad. A cuff is connected between the first end of the sling and the outer layer. The second end of the sling is connected to the outer layer, and an intermediate portion of the sling between the first and second ends of the sling is folded longitudinally into an S-shape so as to provide three plies of the material establishing a second pocket part for retaining an opposite end of the fluid absorbent pad.

5 Claims, 18 Drawing Sheets

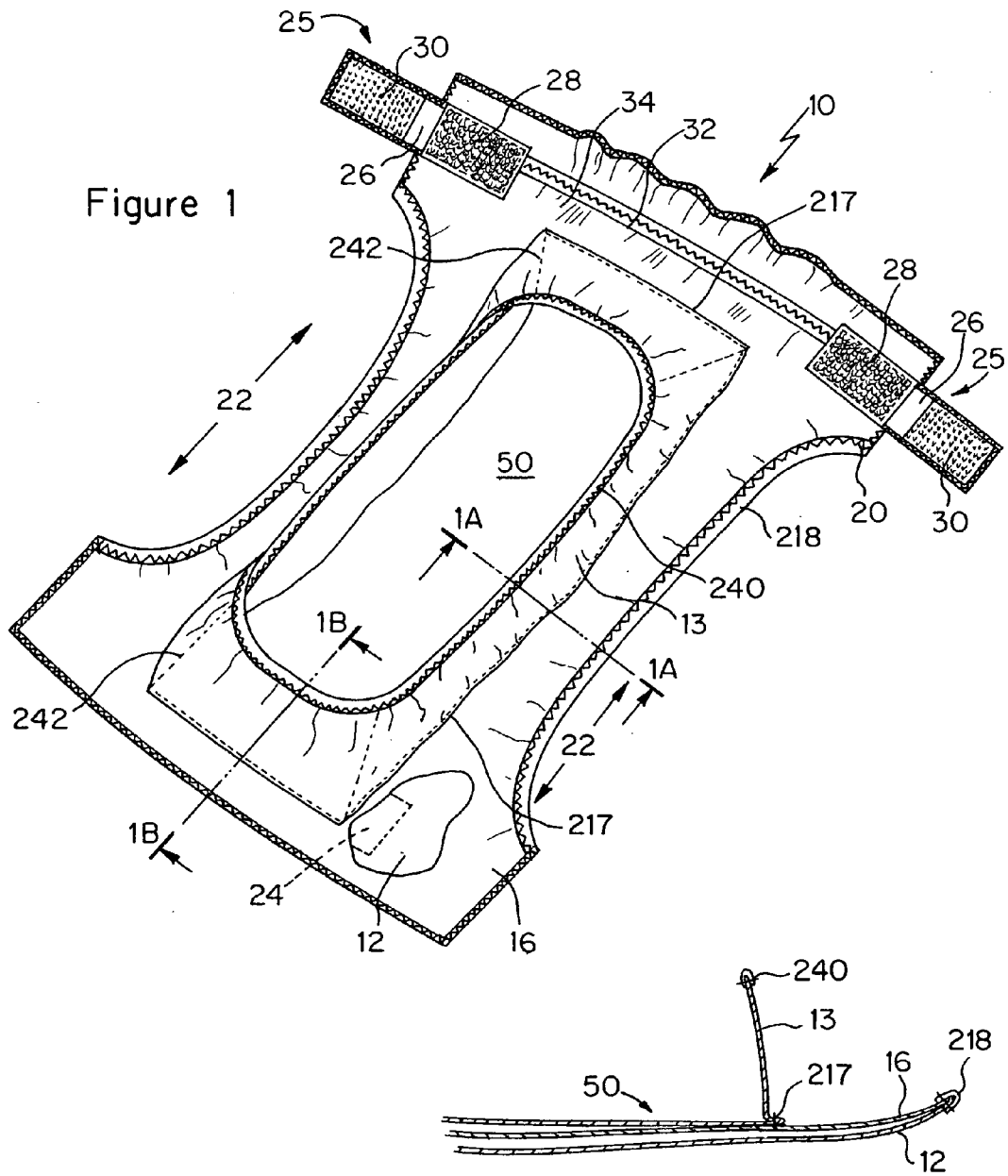
Figure 1
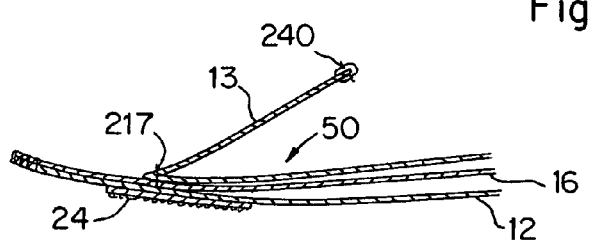
Figure 1A
Figure 1B

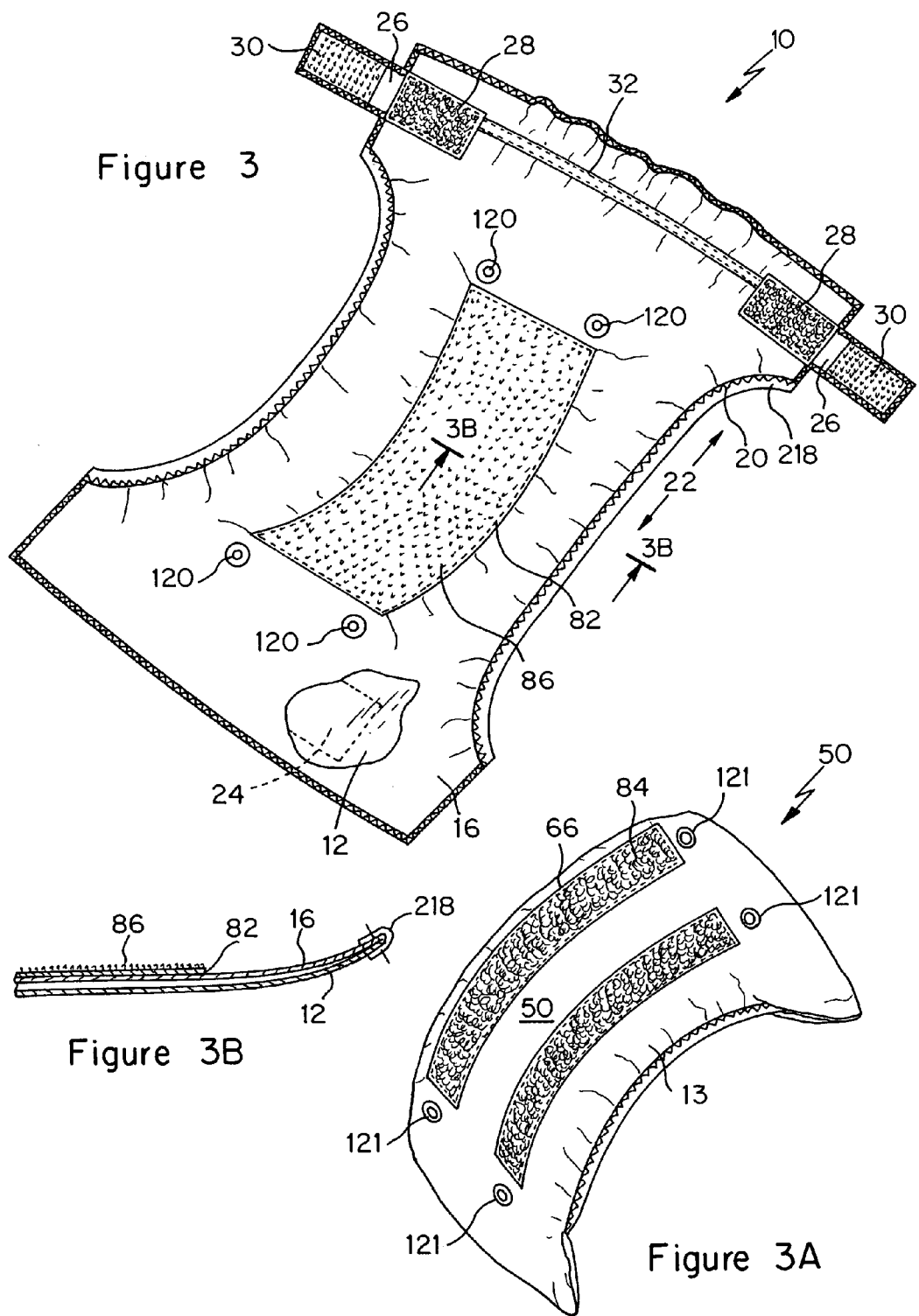

PROTECTIVE UNDERGARMENTS HAVING ANCHORED POCKETED-SLING STRUCTURES AND MANUFACTURING METHODS THEREFOR

RELATED APPLICATIONS

The present application is a continuation-in-part of application Ser. No. 09/512,085, filed on Feb. 24, 2000 now U.S. Pat. No. 6,926,705 that in turn claims the benefit of U.S. Provisional Application Ser. No. 60/121,960, filed on Feb. 25, 1999, both of whose contents are incorporated by reference herein.

FIELD OF THE INVENTION

This invention relates generally to protective undergarments, and more particularly to reusable underwear having, or retrofitted with, novel body fluid containment and fecal matter collection structures.

BACKGROUND OF THE INVENTION

To enhance the fluid and fecal containment properties of protective underwear, U.S. Pat. Nos. 5,137,526 and 5,409,476, issued to Fredrica Coates, describe protective underwear having a waterproof or water-resistant sling with its front and rear ends adjoined through connecting pieces to an outer shell. This sling isolates body fluids from spreading to the outer region of the shell by implementing elastic on the outer perimeter edge of the sling or waterproof gussets mounted on opposite sides of the sling. The elasticized and gusseted sling design is effective, although the volume of fluid able to be contained in this structure is limited.

As an improvement, in U.S. Pat. No. 5,722,127, issued to Fredrica Coates, the sling is enhanced to form a deeper pocket and fasteners of greater adjustability to retain the garment to the wearer. However, even with improved fit and a deeper inner pocketed sling, there still remains a need for a greater circumferential area for fluid and fecal matter containment. Hence, further disclosed in the '127 patent is a pocketed sling for retaining fluid absorbent pads. And Coates application Ser. No. 08/792,735, filed on Jan. 31, 1997, discloses a frontal hidden pocket added to a connecting frontal piece for enhanced circumferential area and hence fluid absorption. However, a need continues to exist for an alternative device for increasing circumferential area for fluid containment. It is also preferred to provide body fluid containment structures, within what will appear to be conventional underwear, particularly desirable for an adult wearer.

There continues to exist a need for more effective protective underwear, and garments for bed wetters or adults, that provide containment while preserving underwear of aesthetic appeal. Prior devices, sewn or heat sealed to garments, are uncomfortable or tend to leak at places in the garment where holes are formed by sewing needles used during assembly.

In accord with an aspect of the invention, a protective undergarment comprises an outer layer of material shaped to conform to buttocks and leg regions of the user, and an elongated sling of material connected to the outer layer, opposite sides of the sling being bowed inward and joined together at a first end of the sling to form a first pocket part for retaining one end of a fluid absorbent pad. A cuff is connected between the first end of the sling and the outer layer, and a second end of the sling is connected to the outer layer. An intermediate portion of the sling between the first and second ends of the sling is folded longitudinally into an S-shape so as to provide three plies of the material establishing a second pocket part for retaining an opposite end of the fluid absorbent pad. At least one or the other of the outer layer and elongated sling is made of a fluid resistant material.

BRIEF DESCRIPTION OF THE DRAWINGS

FIG. 1 is a perspective view showing one embodiment of a reusable diaper with anchor pocketed sling, produced in accordance with the principles of the invention and shown open into position to be worn, including a cutaway portion to expose an underlayer.

FIG. 1A is a cross-sectional view of a diaper with anchored sling, taken along the line 1A—1A in FIG. 1.

FIG. 1B is a cross-sectional view of a diaper with anchored sling taken along line 1B—1B in FIG. 1.

FIG. 3 shows another embodiment of the invention, with fasteners for anchoring a pocketed sling, produced in accordance with the invention with partial cutaway to expose underlying shell.

FIG. 3A shows a removable pocketed sling with an attachment mechanism at the reverse side of the sling.

FIG. 3B is a cross-sectional view of the sling taken along line 3B—3B in FIG. 3.

BEST MODE FOR CARRYING OUT THE INVENTION

Figure 1C:
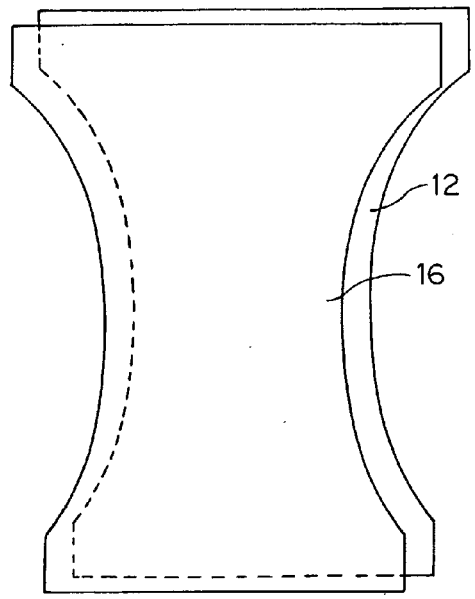
FIG. 1C shows the anchor cloth overlying the outer shell, as a first step in manufacture of the reusable diaper.

Referring to FIGS. 1A–1H, a reusable diaper in accordance with one embodiment of the invention, designated generally by numeral 10, comprises a waterproof or water-resistant (breathable type fabric) diaper shell (outer shell) 12 within which is retained a fluid containment pocket 50, positioned to be located about the groin when worn by an infant or adult. Referring to FIG. 1A, the diaper is formed of three layers; a waterproof or water-resistant outer shell 12, an inner liner 16 generally soft to the touch and optionally of fluid absorbent fabric, and a layer forming a fluid containment pocket, or anchored pocketed-sling, 50 of water-resistant or waterproof material 13. The two outer layers 12 and 16 of the diaper are generally of the same shape, and the anchor cloth 16 is on the inside of, and aligned with, the outer shell 12. This liner 16 forms an attachment mechanism at a stitch line 217 to anchor the pocketed sling 50 to shell 12. The outer shell 12 and its inner liner 16 are joined at the leg hole by a leg elastic strip 218, which convolutes the shell and liner, is stitched at line 20 and holds the shell and liner together to form a leg hole 22. The inner pocketed sling is positioned and attached (stitched) centrally to the inner liner 16 only. Hence, the stitching does not pierce shell 12.

Shell 12 has a fastener 24 of loop-type filamentary material attached to the outer frontal surface of diaper 10. In the rear portion of the outer corners of diaper 10 are fasteners 25, affixed to the diaper 10 such that hook-type filamentary material 30 closes onto loop material 28 to protect the hook material from accumulating lint during laundering, with the hook and loop materials being separated from each other by a space 26 to form a hinge. The elastic strip 32 conforms the layers to fit the waist and buttocks region of the wearer through gathers 34.

Stitch line 242, which may be replaced by heat sealing, assembles the corners of the pocket. This assembly may also be accomplished by folding the corners 21 inward to the reverse side, and then sealing to establish an inside seam.

Referring to FIG. 1A, which is a cross-sectional view of outer layer 12 connected to the inner layer 16 at elastic strip 218, stitch line 217 adjoins pocket 50 to the inner liner 16A. Elastic trim 240 forms an adjustable pocket opening to receive fluid into a fluid absorbing pad (not shown). Stitch line 242 connects the corners of the pocket 50, as previously described, and the pocket is bounded by elastic strip 240 to present a smooth finished surface to contact the wearer.

FIG. 1B is similar to FIG. 1A, but depicts the presence of loop-type filamentary material 24 positioned on the outer surface of shell 12. The loop material 24 fastens the garment to the wearer when hook tabs 30, shown in FIG. 1, close onto the front of the garment.

Figure 1D:
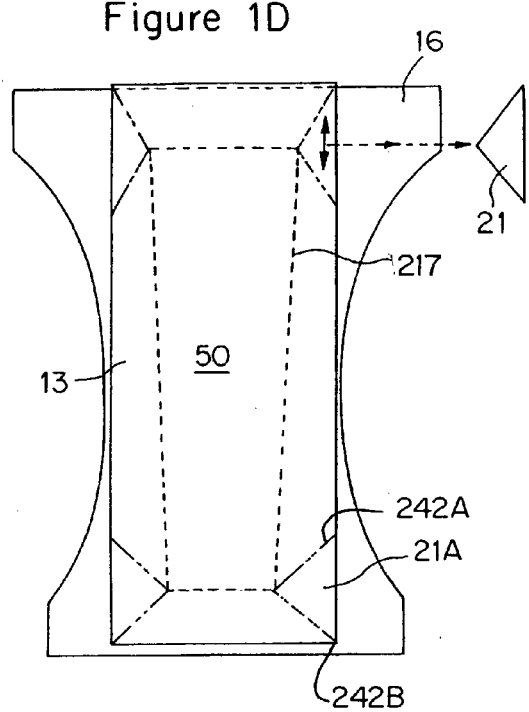
FIG. 1D shows the anchor cloth with a mounted pocket sling, together with cutting away of the corner of the pocketed sling.

FIGS. 1C–1H show the construction method by which three layers of fabric come together to form a leak proof undergarment interior. In FIG. 1C, a piece of anchor cloth 16 is positioned over outer shell 12, similarly configured, as a first step in the manufacture of anchored pocket 50. In FIG. 1D, stitch line 217 pierces the cloth 16 in a rectangular pattern and attaches to hold pocket 50 to its anchor cloth now stitched centrally. The edges or sides of the material 13 take shape into a pocket-shape 50 as corners 21 are removed, and the sides become ready for seaming at lines 242A, B. The pocket may alternatively take shape by folding the corners at 242A and 242B, i.e. the cover portion 21A would not be removed.

Figure 1E:
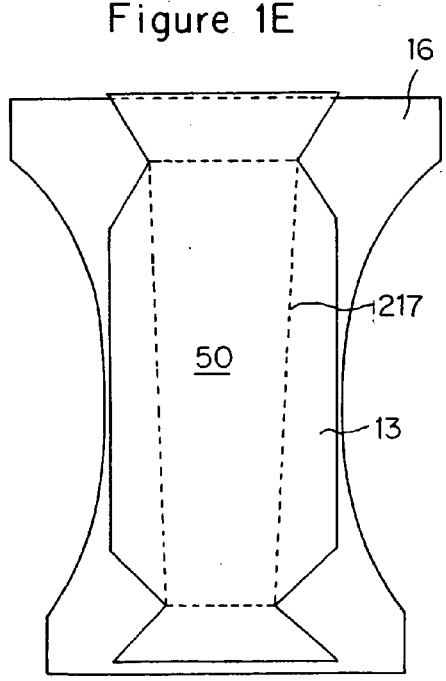
FIG. 1E is a view of the pocketed sling, with the four corners of the pocket removed.
Figure 1F:
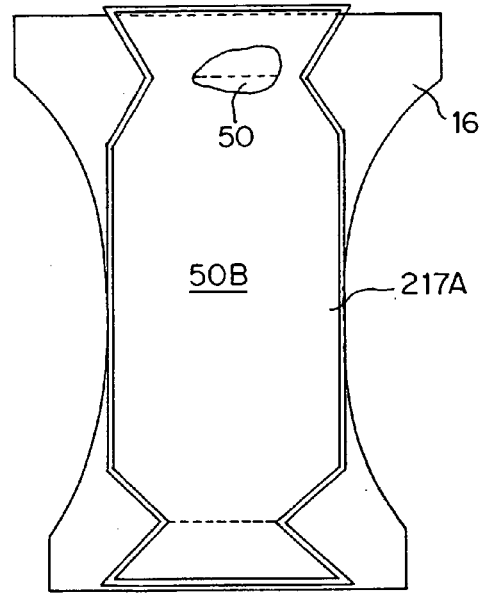
FIG. 1F shows a double pocket sling, where a second pocket is formed and anchored by a first anchored pocket.

In FIG. 1E, bulk is advantageously reduced in the garment by removing the triangular corners at 21A shown in FIG. 1D. In FIG. 1F, an additional piece of fabric at 50B is optionally added at stitch line 217A (for either waterproof or absorbing purpose) at pocket 50 as it overlays the stitch line 217 of the primary pocket 50.

Figure 1H:
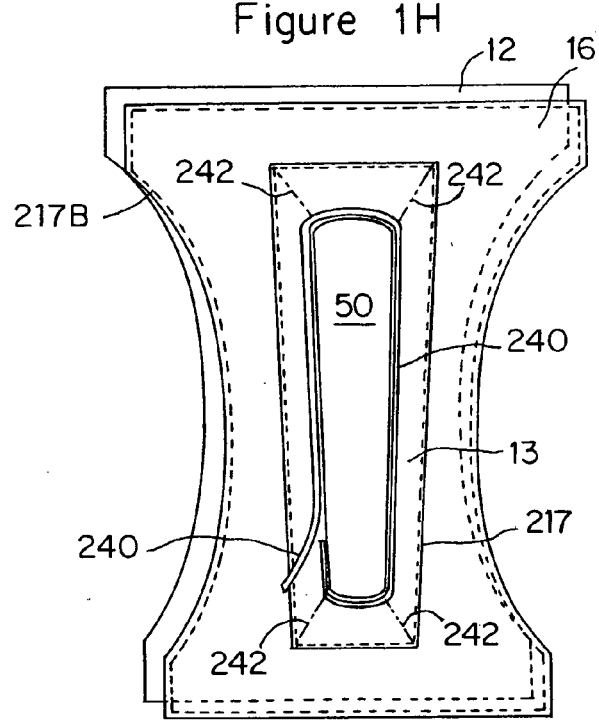
FIG. 1H shows assembly of an anchored pocket sling to the anchor cloth overlying a shell.
Figure 1G:
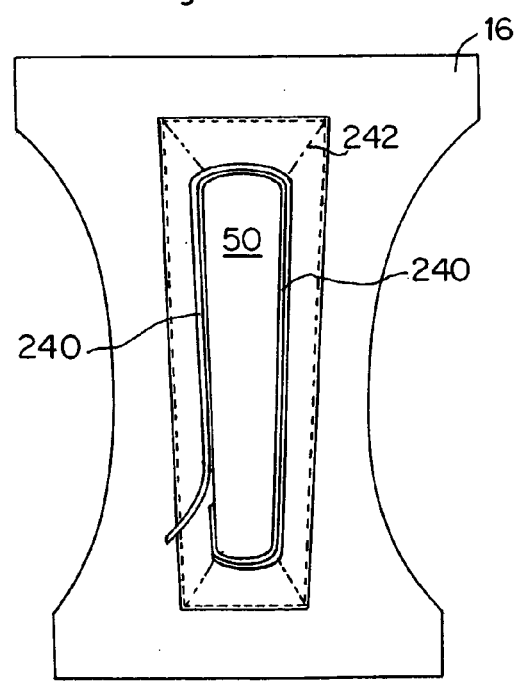
FIG. 1G shows the four corners of the pocketed sling joined and formed with pocket edge covered by an elastic.

In FIG. 1G, pocket 50 is now formed as seamed, joined or heat sealed at stitch lines 242, so as to keep the pocket sides properly shaped, and with elastic 240 convoluting the edge of the pocket.

In FIG. 1H, the three layers are now in position to be joined at stitch line 217B. The layers are held together for assembly of the garment to its fasteners and leg hole elastic strips, as seen in FIGS. 1, 1A and 1B.

Figure 2:
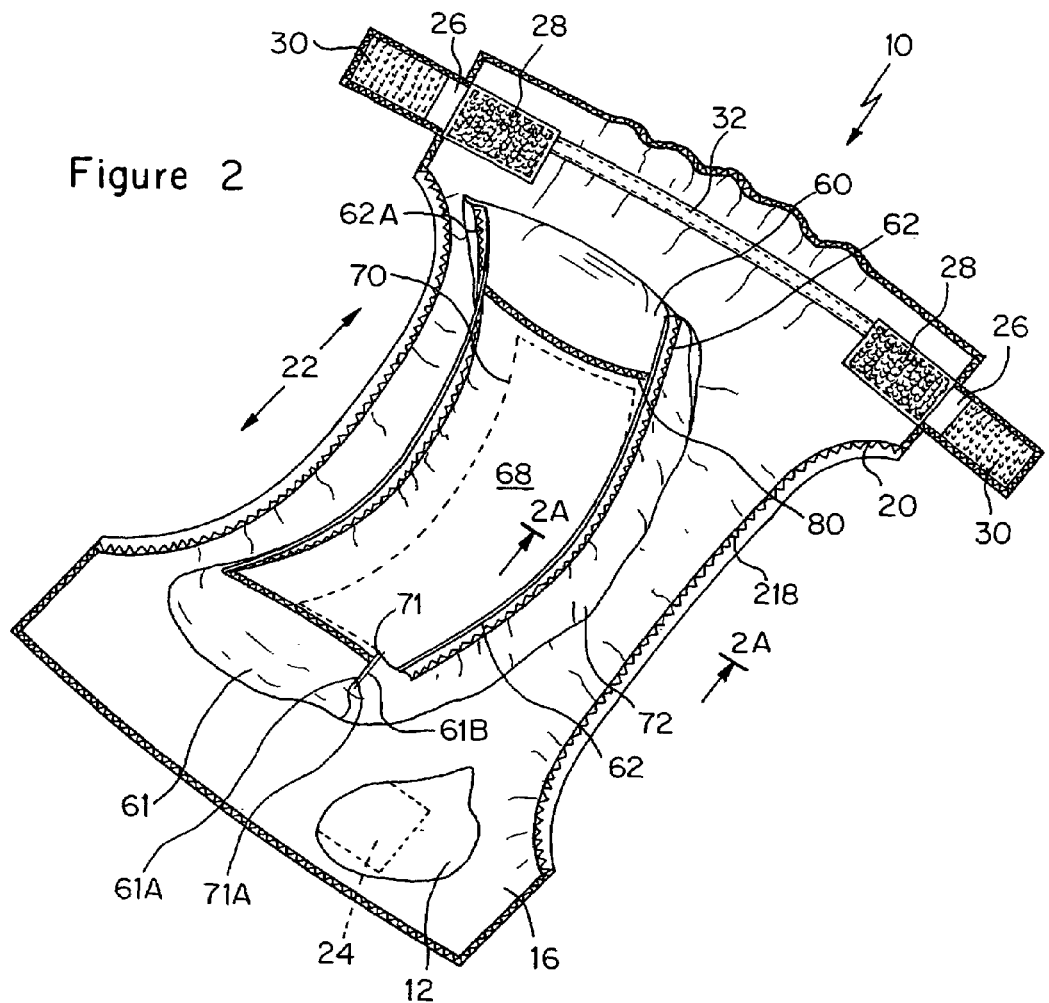
FIG. 2 is a perspective view showing another embodiment of the invention with anchor pocket sling having extended cuffed pockets, with partial cutaway to expose underlying shell.

Refer now to FIG. 2, depicting another embodiment of the invention, in which the outer shell is the same, but sling configuration different compared to the embodiment of FIG. 1. In FIG. 2, diaper 10 is again composed of three layers; outer layer 12 of water-resistant material, inner layer, or anchor cloth, 16 that is not water-resistant and an inner fabric 72 cuffed to form pocketed sling 68 of water-resistant material. The rectangular pocketed sling 68 has folded fabric 72 at end cuffs 60 and 61, the rear end cuff 60 being formed by folding outer perimeter edge 80 of fabric 72 inward, and the two edges of the fold inserted into elastic strip 62. Elastic strip 62 extends longitudinally to frontal cuff pocket 61, where folded edge 61A joins outer pocket edge 71 at seam line 71A. The frontal pocket 61 is formed from the cuff as edge 71 joins with edge 61A at seam line 71A on the interior side of the cuff. Cuff pocket 60 is formed in the rear portion of the diaper by adjoining folded edges within the elastic The rear cuff outer corner may be stitched down at stitch line 62A. The entire pocketed-sling 68 is attached to anchor cloth 16 in the central portion of diaper 10 at stitch line 70, which forms a stabilizing rectangular attachment of cuffed pocketed-sling 68 to its anchor cloth 16. Leg hole 22 and fasteners 24 and 26 are identical to those depicted in FIG. 1.

Figure 2A:
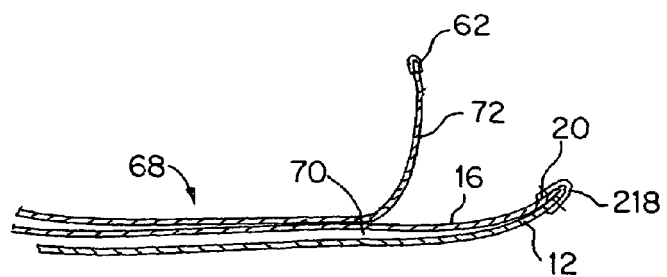
FIG. 2A is a cross-sectional view of the diaper of FIG. 2, with anchored pocketed-sling and extending cuff pockets, taken along line 2A—2A in FIG. 2.

Referring to FIG. 2A, which is a cross-sectional view of pocket 68, outer layer 12 is connected to inner layer 16 at elastic trim 218, and held fast by zig-zag or straight stitching at 20.

Figure 2B:
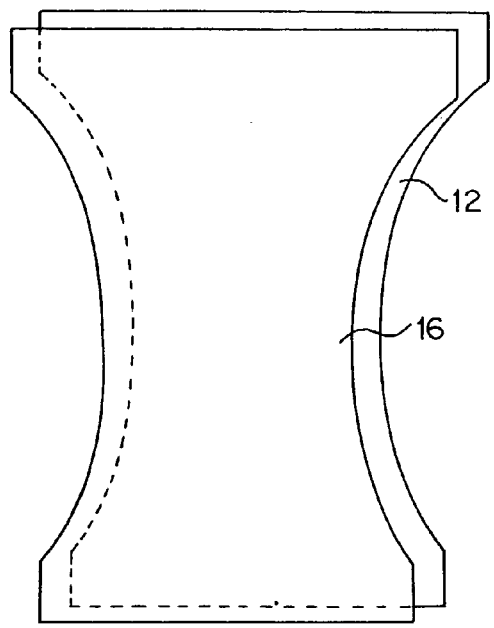
FIG. 2B is a plan view of the anchor cloth overlying the shell cloth.
Figure 2C:
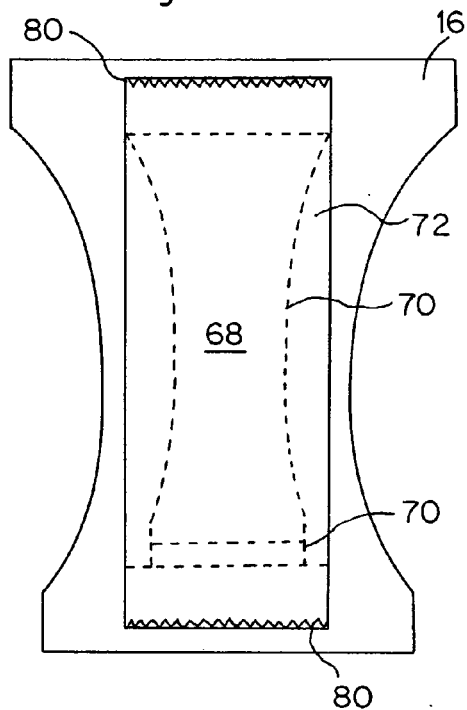
FIG. 2C shows the anchor cloth with mounted fabric piece to form a cuffed pocketed sling.

Manufacture is carried out first by overlaying cloth 16 on waterproof cloth 12 as its liner, as shown in FIG. 2B. In FIG. 2C, liner 16 and fabric piece 72 are stitched in an hourglass fashion at 70 to anchor cloth 16. Opposite ends of waterproof fabric piece 72 are overlock stitched at 80.

Figure 2D:
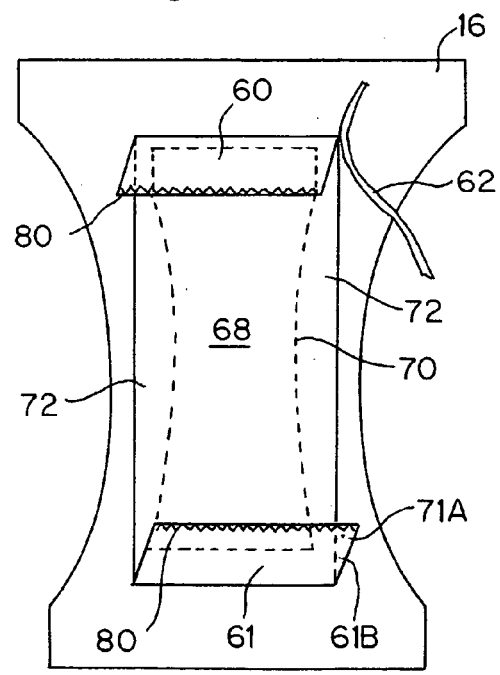
FIG. 2D shows mounting and folding of the cuffed pocketed sling on its anchor cloth.

FIG. 2D shows the opposite ends being folded inward to form cuff 60 and folded backward forming cuff 61. At cuff 60, the folded sides will meet and be encased in elastic strip 62, bending the wall of fabric 72 inward. The opposite end of the cuff is formed in a different fashion, as end 80 of cuff 61 is folded backward, and the two raw edges 61A and 71 are encased in elastic strip 62. Optionally, the elastic may be omitted as a finished edge of the frontal pocket 61 is formed by seam line 71A rather than elastic 62.

Figure 2E:
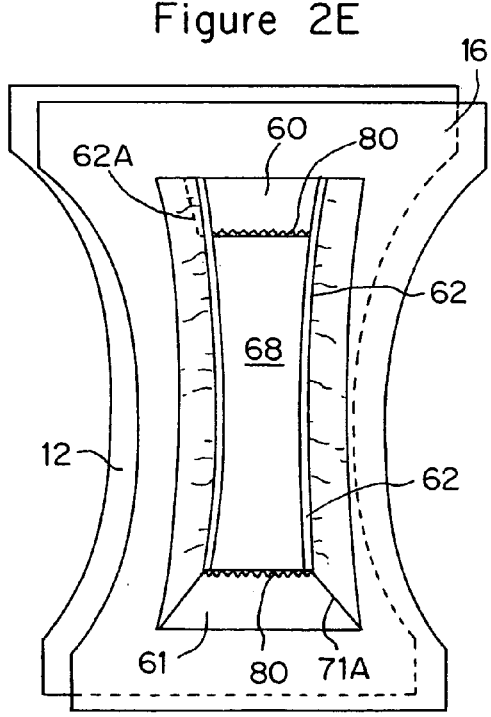
FIG. 2E shows assembly of a cuffed pocketed sling to the anchor cloth and shell.

In FIG. 2E, the cuff is reversed and seam line 71A is flush with edges 61A and 71, and elastic 62 is now on the inside of pocket 68. Optionally, a tacking 62A can be added to hold elastic down at cuff 60. The formed pocket 68 adjoined to cloth 16, overlies outer shell fabric 12, and is ready for assembly as a garment of protective underwear.

In another embodiment of the invention, depicted in FIG. 3, diaper 10 is composed of two layers, with liner 16 and shell 12 connected at elastic strip 218 by stitching 20. The absorbing pocketed-sling 50 of FIG. 1 is detachable through an optional fastener material, such as Velcro® material in the form of a rectangular sewn piece 86, or alternatively as snaps 120. In FIG. 3B, the Velcro® fastener is mounted at line 82 on anchor cloth 16, whereas in FIG. 3A, the pocketed sling 50 is shown detached from its anchor cloth to expose the underlying attachment. Examples are snaps 121 to be matched within 120 of FIG. 3 when coupled for use, or Velcro® fastening strips 84 stitched at 66 for coupling with complementary Velcro® strip 86, stitched at 82. Both Velcro® fastening strips 66 and snaps 121 are shown, for illustrative purposes, although in practice only one or the other would be implemented.

Figure 3C:
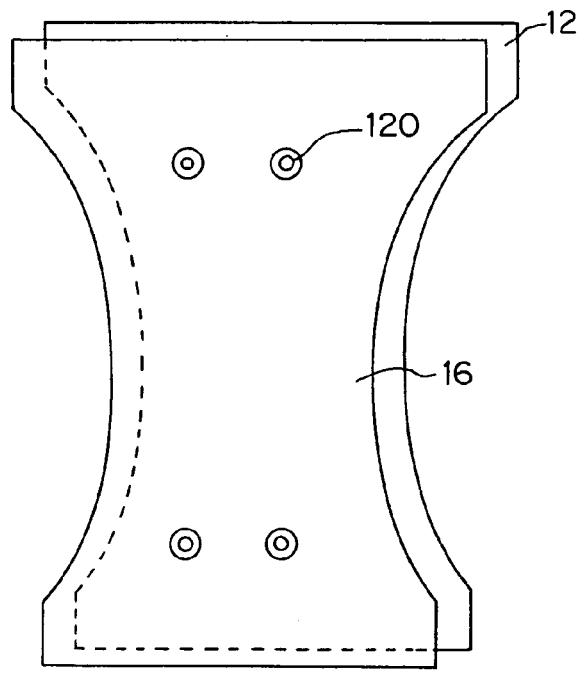
FIG. 3C shows the anchor cloth with a snap attachment for the pocketed sling structure.
Figure 3D:
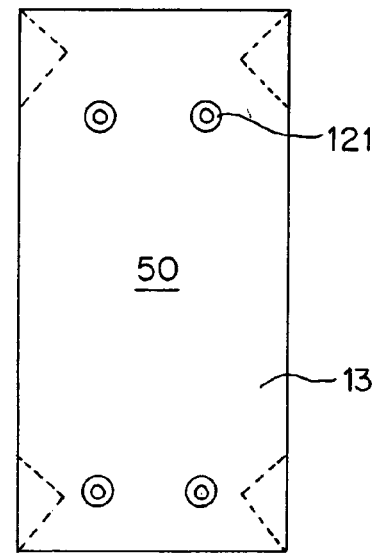
FIG. 3D shows a pocketed sling cloth with corresponding snap attachment mechanism.
Figure 3E:
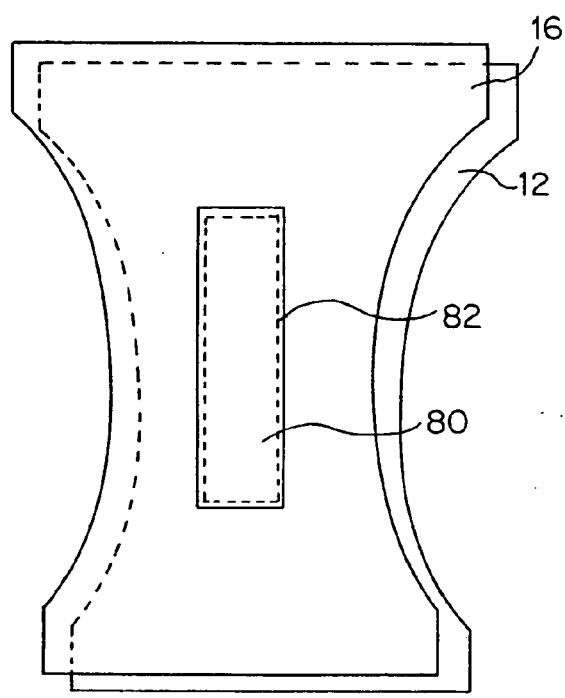
FIG. 3E is a view of the anchor cloth having a Velcro® fastening attachment mechanism.
Figure 3F:
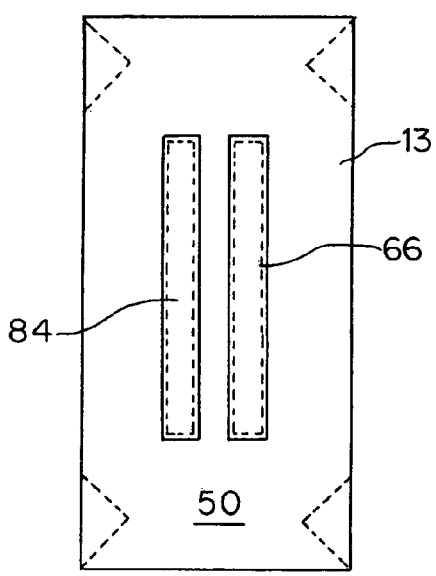
FIG. 3F shows the pocketed sling cloth with corresponding Velcro® attachment tabs.

FIGS. 3C–3F show optional placement of the fastening means for enabling the pocketed sling to be detached from its anchor cloth. FIG. 3C shows the mounting of four male snaps 120 overlying shell 12, FIG. 3D the pocket piece 50 with corresponding female straps 121, and FIG. 3E Velcro® loop material mounted on anchor cloth 16 overlying cloth 12. And in FIG. 3F, a pocket 50 is formed with hook fastener strip 84 stitched at 66 to be coupled with a rectangular member 86 when the pocket is fully formed, as shown in FIG. 1, where attachment is stitching.

Figure 4:
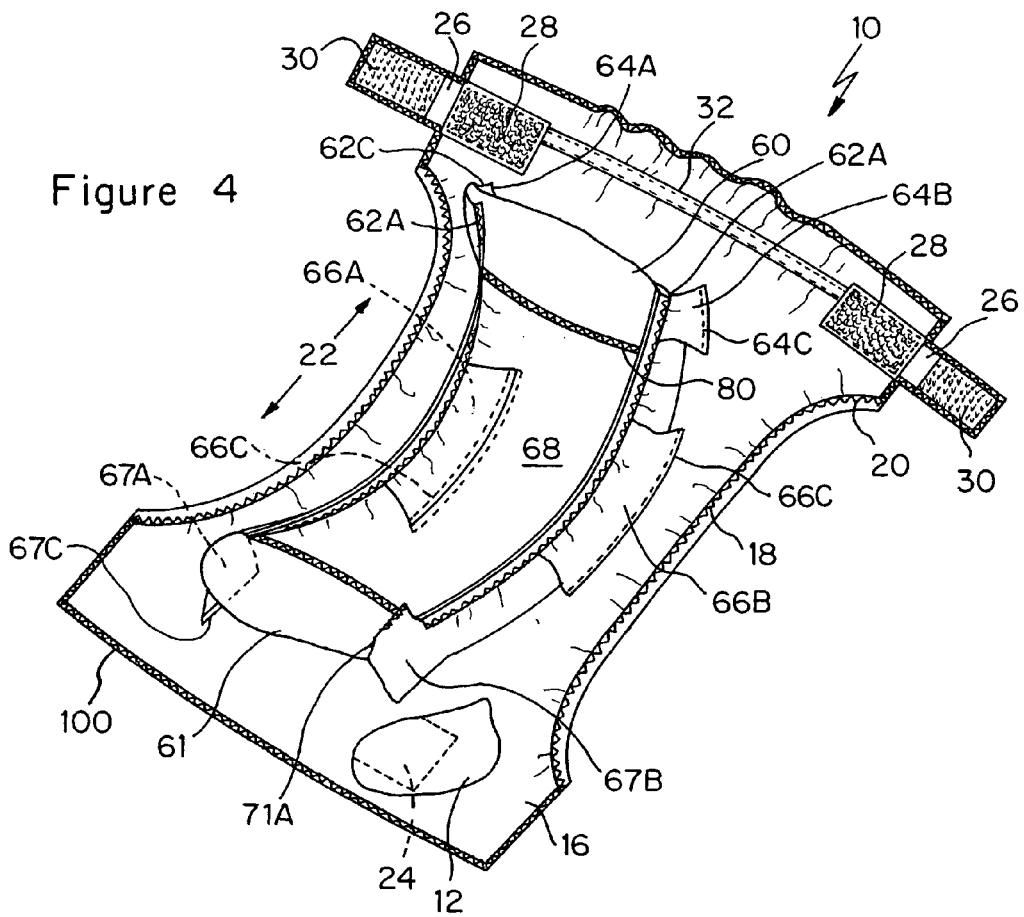
FIG. 4 shows another embodiment of an anchored sling and strip anchors, produced in accordance with the invention, with partial cutaway to expose underlying shell.
Figure 4A:
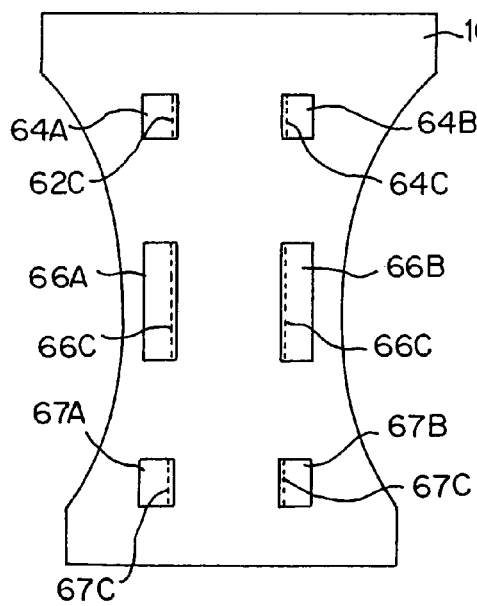
FIG. 4A shows the anchor cloth with attached strips in position to hold the pocket.
Figure 4B:
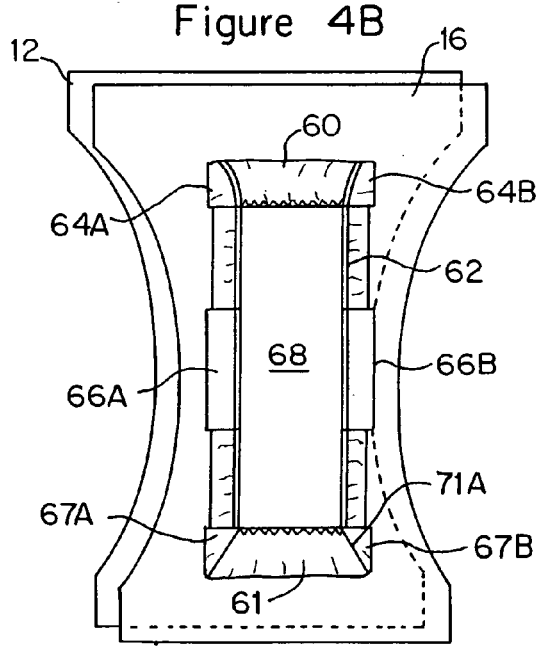
FIG. 4B shows a mounted pocket sling, held by anchor strips on an anchor cloth and overlying shell cloth.

In another embodiment, depicted in FIG. 4, diaper 10 is composed of two layers of fabric: an inner liner cloth 16 overlying a shell 12. The pocketed sling device, which as depicted is similar but not identical to the types shown in FIGS. 1–3, is now anchored to the liner cloth 16 with strips of fabric 64A, 66A, 67A, positioned on one side of the anchor cloth 16, and on the opposite side anchor strips 64B, 66B and 67B are positioned to hold and stabilize the pocket. In this figure, the anchor strips are each tacked to the anchor cloth 16; 64A is tacked at 62C, 66A at 66C, 67A at 67C, 64B at 64C, 66B at 66C and 67B at 62B. As the first step in the stabilization of pocketed sling 68, FIG. 4A shows the tacking on the anchor cloth 16, and in FIG. 4B the strips each bend inward into the elastic strip 62 as the pocket is formed. Just as in FIG. 2, elastic strip 62 is exposed at cuff 60, but not at cuff 61. Hence, strips 64A and 64B are inserted in the elastic 62 at one end and at the opposite end strips 67A and 67B are inserted in the seam 71A with elastic 62 on the underside of cuff 61, holding the seam together.

Figure 5:
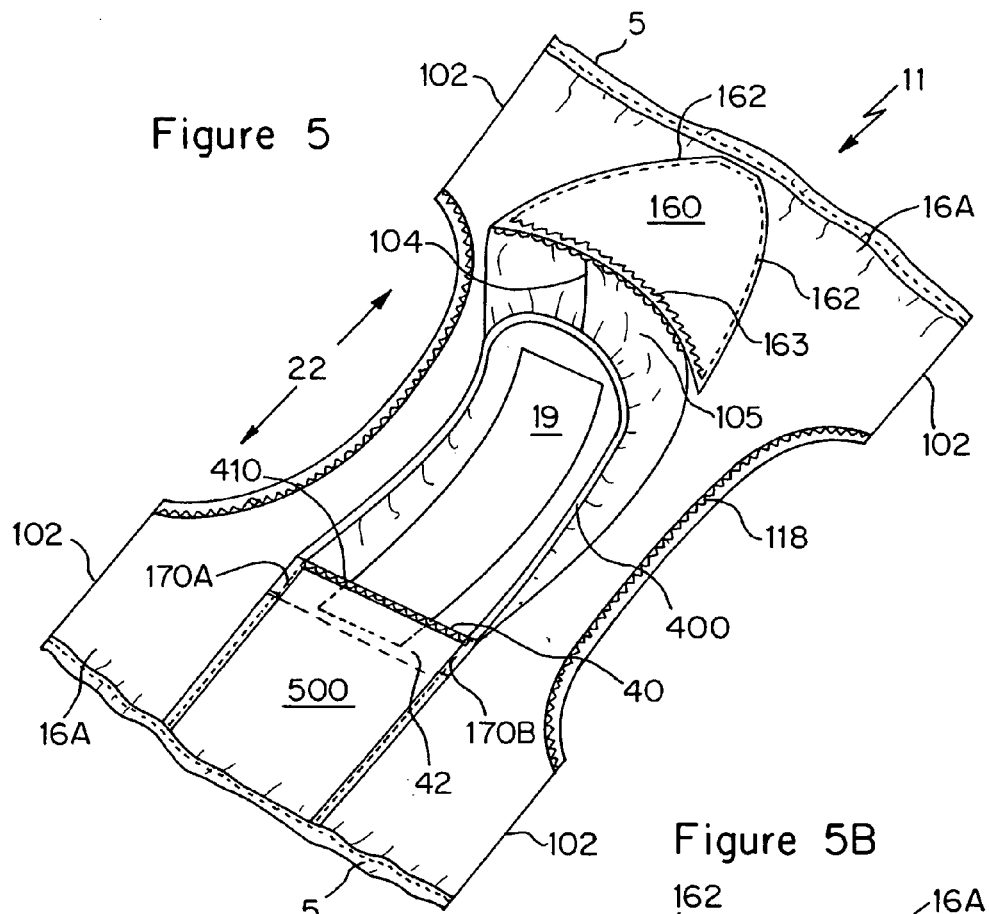
FIG. 5 depicts another embodiment of the invention in which an underpant is fitted with a pocketed sling.

In another embodiment, depicted in FIG. 5, the (anchor) liner cloth 16 of the previously described embodiments now becomes 16A, the waterproof or fluid-resistant outermost surface of protective underwear diaper to which pocketed sling 500 of a waterproof or water resistant material is stabilized before side seams 102 of the cloth 16A are joined together (not shown) to form the diaper or pant (panty). This cloth 16A could also be of a non-waterproof or non-fluid-resistant material like that of a traditional lady's panty or a man's jockey pant.

Still referring to FIG. 5, an anchor cuff 160 of preferably triangular shape attaches to cloth 16A. This cuff 160 is held to the cloth 16A, in a triangular stitch pattern 162. At the widest end of the triangular cuff 160, pocketed sling 500 is attached at line 163 by an overlock finishing stitch. This may be stitched on the underside or topside of the sling 500. Leg hole 22 is covered by elastic 118. An elastic strip 5 finishes the frontal and rear edges of the garment 11.

In the rear portion of the garment, pocketed sling 500 is stabilized with stitching 170A, 170B on opposite sides of pocket 500. The stitching anchors the waterproof sling 500 to the cloth 16A. The resulting design is most advantageous for the wearer who needs protection in the rear portion of the garment.

Figure 5A:
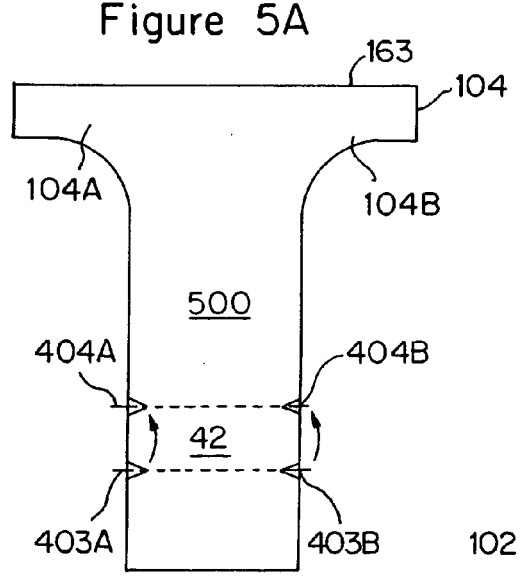
FIG. 5A shows the pocket sling structure of FIG. 5.
Figure 5B:
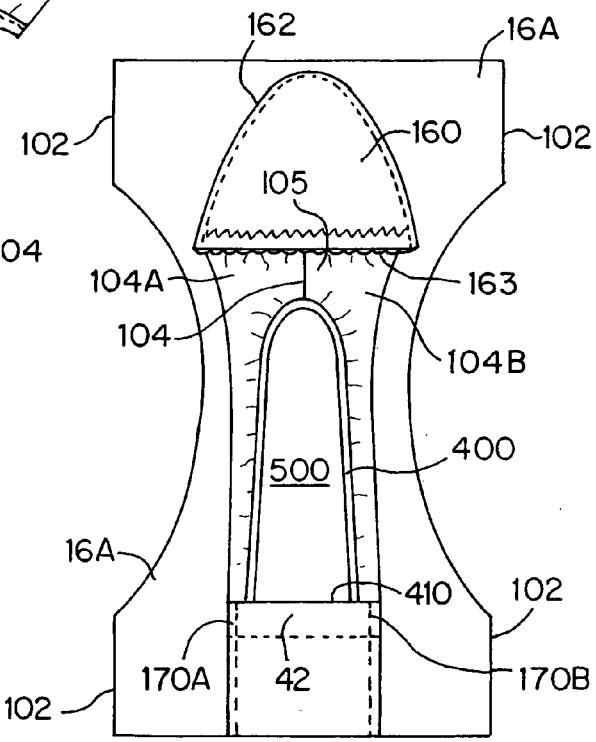
FIG. 5B is a view of the frontal cuffed anchor piece attached to a pocketed sling attached to the underpant.

In FIG. 5, frontal sidewalls 104A, 104B of pocketed sling 500 shown in FIG. 5A are brought together at line 104 to form a frontal pocket portion 105. This process of forming the pocketed sling 500 is seen in FIGS. 5A and 5B. In FIG. 5A, the shape of sling 500 is formed as sides 104A and 104B are folded inward, centrally and joined at line 104 by creating a seam in FIG. 5B. Elastic strip 400 is applied to fit the groin of the wearer as pocketed sling 500 becomes elasticized around the pubic area. A rear pocket portion 42 of pocketed sling 500 is formed as the rectangular fabric piece folds at notches 403A and 403B on opposite and parallel sides of the rectangular piece of fabric. The fold defined by line 403A–403B becomes a permanent crease line 410 when the fold is top stitched. The crease line 410 may also be an overlock stitch. Once crease line 41 is folded inward (upward in the figure) to notches 404A and 404B as shown by the arrows in FIG. 5A, top stitching 170A and 170B holds the outer sides of pocket portion 42 together. As shown in FIG. 5, a fluid absorbent pad 18 may now be held in the rear portion of the garment by the fluid-tight pocket portion 42. Elastic 40 may be applied to enhance the cupping action of formed pocket portion 42 as it holds one end of pad 18. The as the pad resides on top of a first ply of fabric of single thickness and the rectangular piece of fabric is wrapped around the end of the pad to become a second ply of fabric. The remainder of the pocket 42 is suspended by a third ply of the fabric folded backward and attached to the garment establishing a continuous S-shaped fabric configuration in cross-section in the longitudinal direction of the pocketed sling 500. The third ply of fabric faces the skin of the wearer while suspending the rear portion of a fluid-tight pocket.

Figure 6:
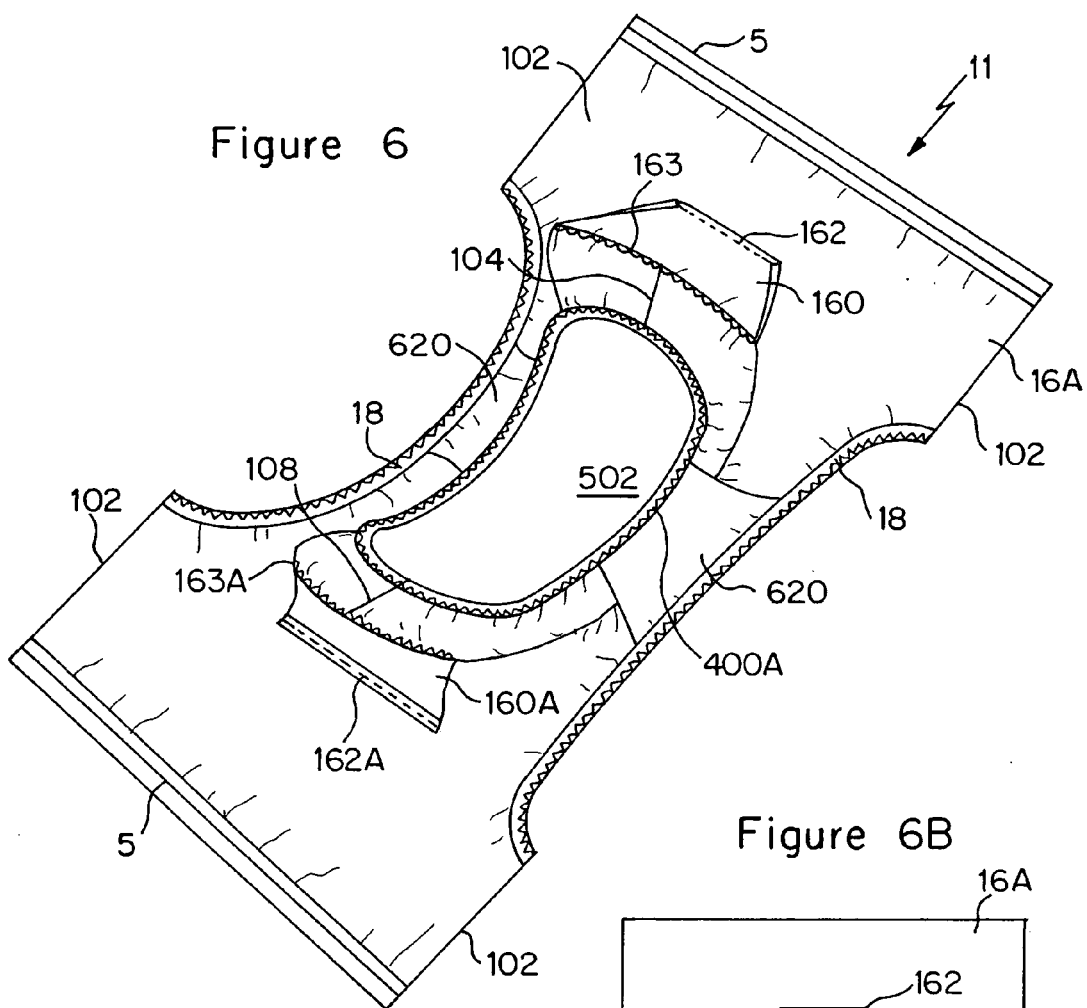
FIG. 6 is a view of another embodiment of ladies' or men's underpant, with a pocketed sling anchored by an anchor cuff in both frontal and rear portions of the garment.

FIG. 6, another embodiment of similar structure to FIG. 5, incorporates the same elements of structural formation; outermost surface layers 16A forming as both a panty and anchor cloth for a pocketed sling, the same elastic 5 for finishing outer waist portions of the garment, and side seams 102, that, when seamed form protective panty 11. The anchored pocket 502 of FIG. 6 is, at stitch lines 163, 163A, attached to central connecting pieces 160 and 160A respectively at frontal and rear portions, now stitched centrally to 16A at stitch line 162 and, 162A respectively. Anchor strips 620 are inserted in both sides of leg hole, elastic 18 at central portion of leg hole elastic 18 and then connected, or inserted in, pocket elastic 400A. Manufacturing of garment strips 620 may be in reverse order of assembly by first inserting in pocket elastic 400A and then attaching to the central portion of the panty (stitched over the top of elastic 18). These connecting pieces 620 anchor the pocket 502 without piercing the fluid absorbing or containing area of pocket 502. The connecting pieces suspend the pocket 502 centrally at opposite ends. The pocket 502 is connected by overlock stitching (not shown). Elastic 18 finishes the leg hole. Elastic 400A terminates within seam 104 and seam 108, and the outermost edges of the pocket are finished by an overlock stitch at stitch lines 163 and 163A.

Figure 6A:
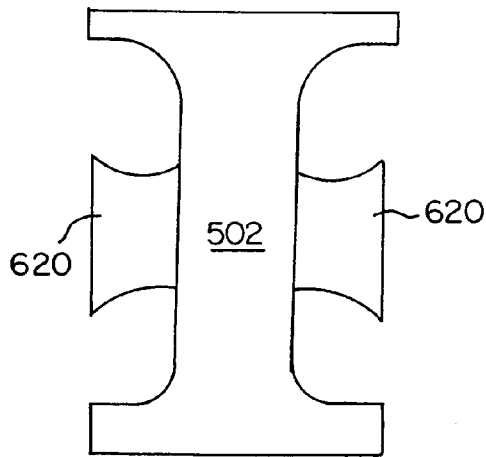
FIG. 6A is a view of the pocketed sling structure of FIG. 6.

In FIG. 6A, pocket 502 shows the attachment of side anchor strip 620.

Figure 6B:
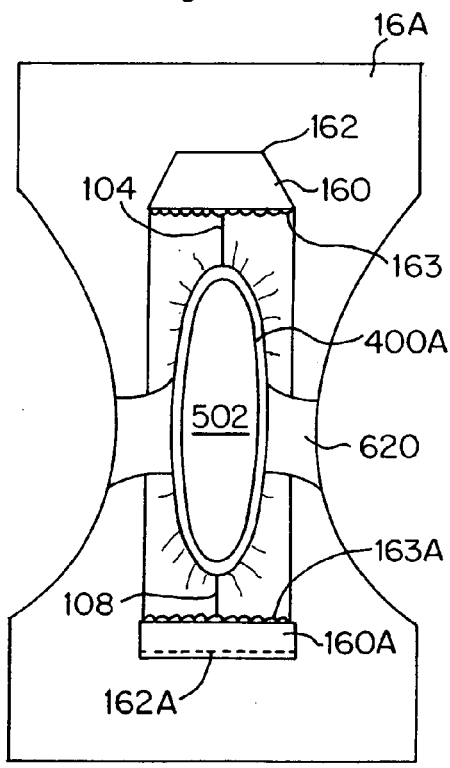
FIG. 6B shows the cuff anchor piece attached to an anchored pocket, attached to the underpant fabric as an anchor cloth.

In FIG. 6B, center anchor pieces 620 are now encased in elastic 400A.

Figure 7:
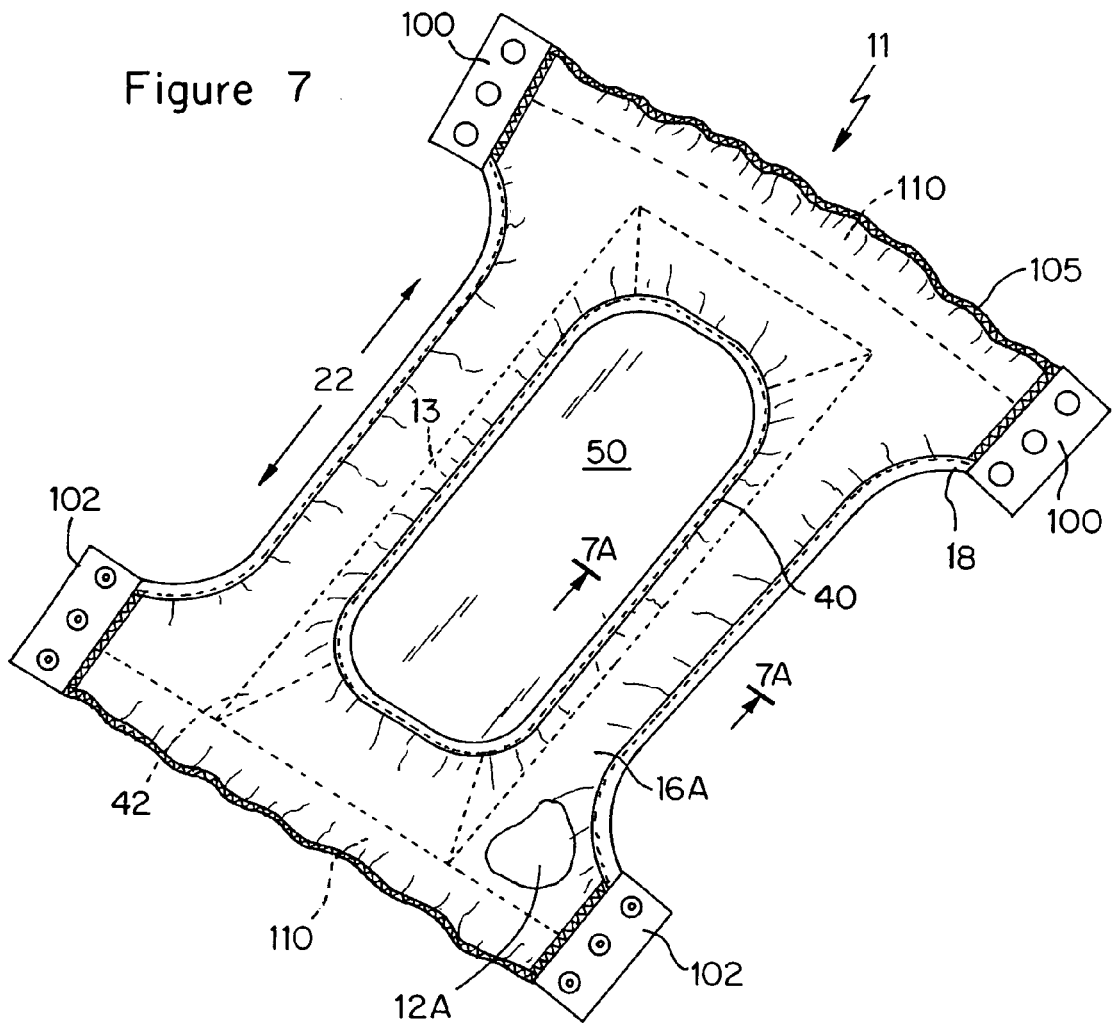
FIG. 7 is a plan view of an embodiment of a reusable diaper having snaps, with a submerged pocket sling produced in accordance with the principles of the invention, and opened in position to be worn, with partial cutaway to expose underlying shell.

In FIG. 7, there is yet another embodiment of an anchored pocket sling. This embodiment is identical to FIG. 1 with the exception that the pocketed structure is attached, suspended below the anchor cloth 16A, therefore, the pocket 50 resides between the shell 12A and anchor cloth 16A.

FIG. 7 also depicts side snap fasteners for fastening sides of garment together for wearing. Side snap fasteners 100, 102 are used in this garment as an alternative to Velcro® fasteners shown in earlier figures.

Waist elastic 110 is also positioned beneath anchor cloth 16A, so as to protect the skin of a wearer in the event that the elastic may be wide and need fabric over it. Overlock stitching 105 connects 16A with outer shell 12A at the outermost edge of the garment.

Figure 7A:
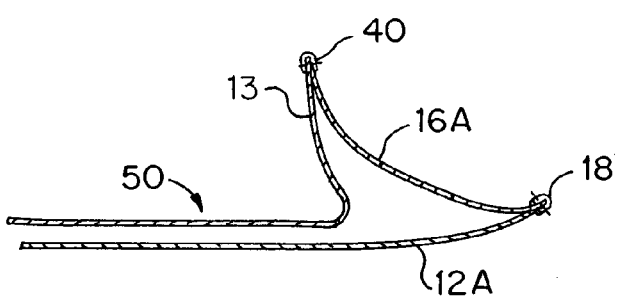
FIG. 7A is a cross-sectional view of a diaper taken along line 7A—7A of FIG. 7.

In FIG. 7A, pocket 50 is suspended between anchor cloth 16A and shell 12A. Elastic 40 holds pocket perimeter edge with anchor cloth circular edge.

Figure 7B:
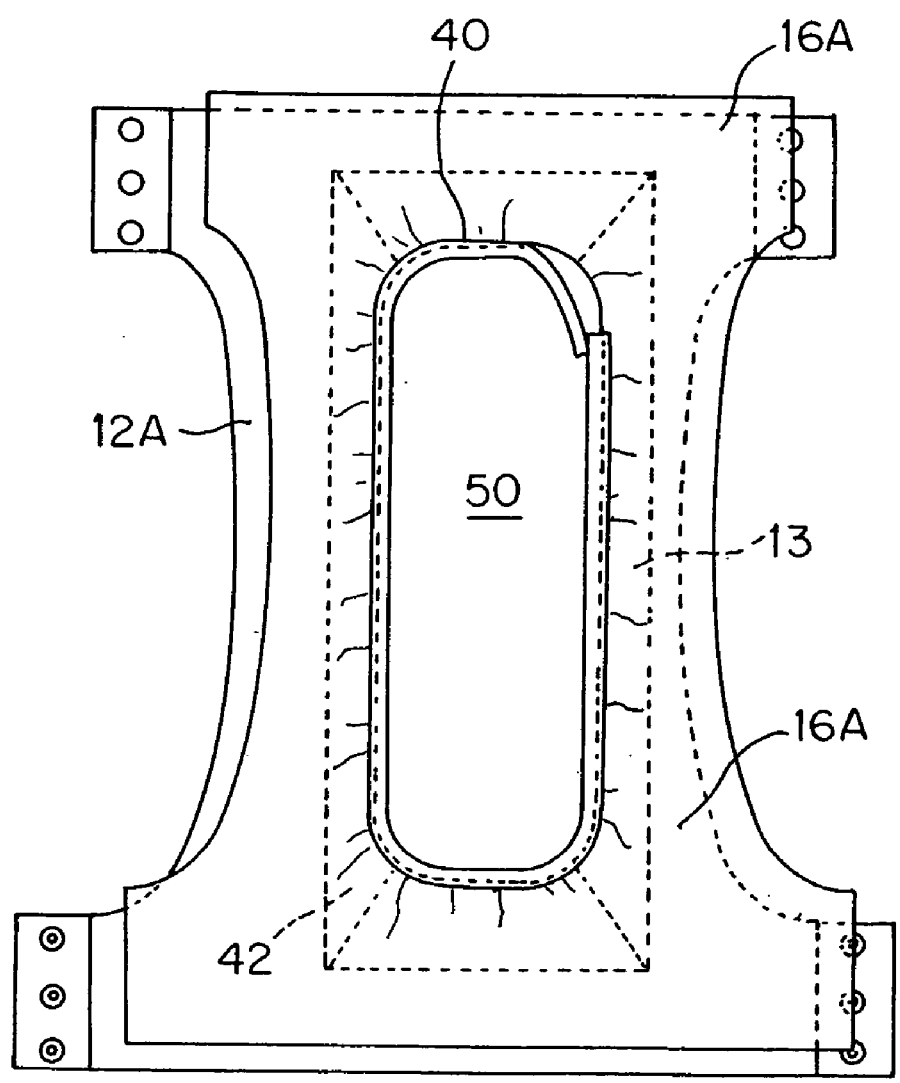
FIG. 7B shows an anchor cloth holding the submerged pocket, with pocket attached on the underside of the anchor cloth and overlying a shell cloth with snap fasteners.

In FIG. 7B, on the underside, dotted lines represent the now suspended and floating pocket, 50, of same structure as pocket 50 of FIG. 1. It is a hidden pocket, suspend by the joining of pocket 50 to anchor cloth 16A at elastic 40. Sides 42 are joined as in FIG. 1, but no stitch line 17 is necessary in this embodiment as the base of the pocket floats. This feature further enhances the waterproof property of the pocket.

Figure 8:
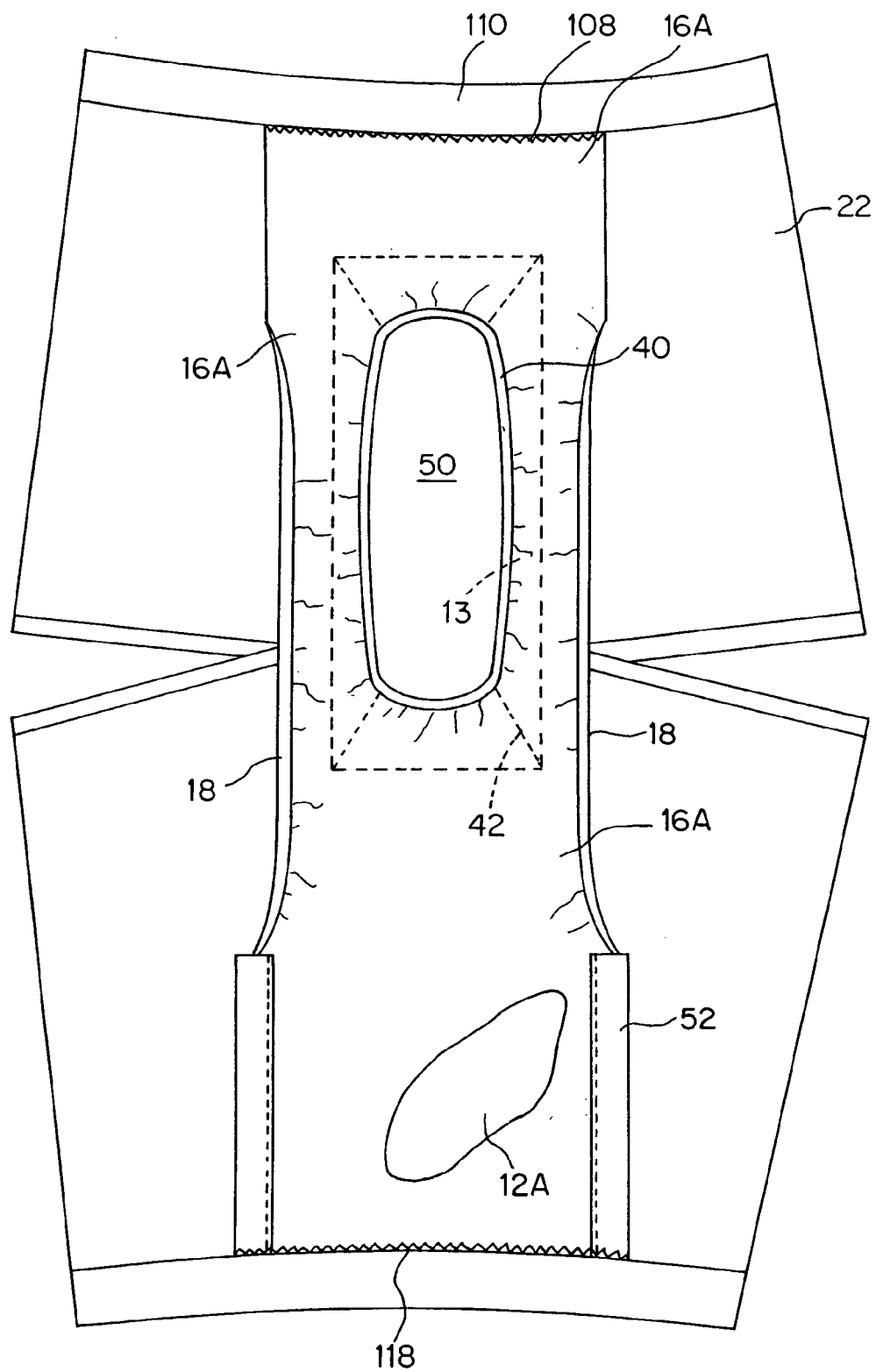
FIG. 8 is a plan view of another embodiment of a man's boxer underpant, open at its side seams, laid flat with a submerged pocket-sling structure retrofitted and produced in accordance with the principles of the invention, with partial cutaway to expose underlying shell.

In FIG. 8 the submerged pocket structure of FIG. 7 is applied to a male boxer short 22. The submerged pocket 50 includes the principles of the invention disclosed in FIG. 6 including submerged pocket 50, with seamed walls 42, suspended between anchor cloth 16A and waterproof piece 12A held on opposite sides by elastic 18. The addition to this variation of the invention is anchor strip 52 which stabilizes the protective sling in the rear portion of boxer short 22. Boxer short 22 has an elastic waist 110 and a sling device with submerged pocket 50 held to central frontal interior portion of boxer pant 22 at stitching 118.

Figure 9:
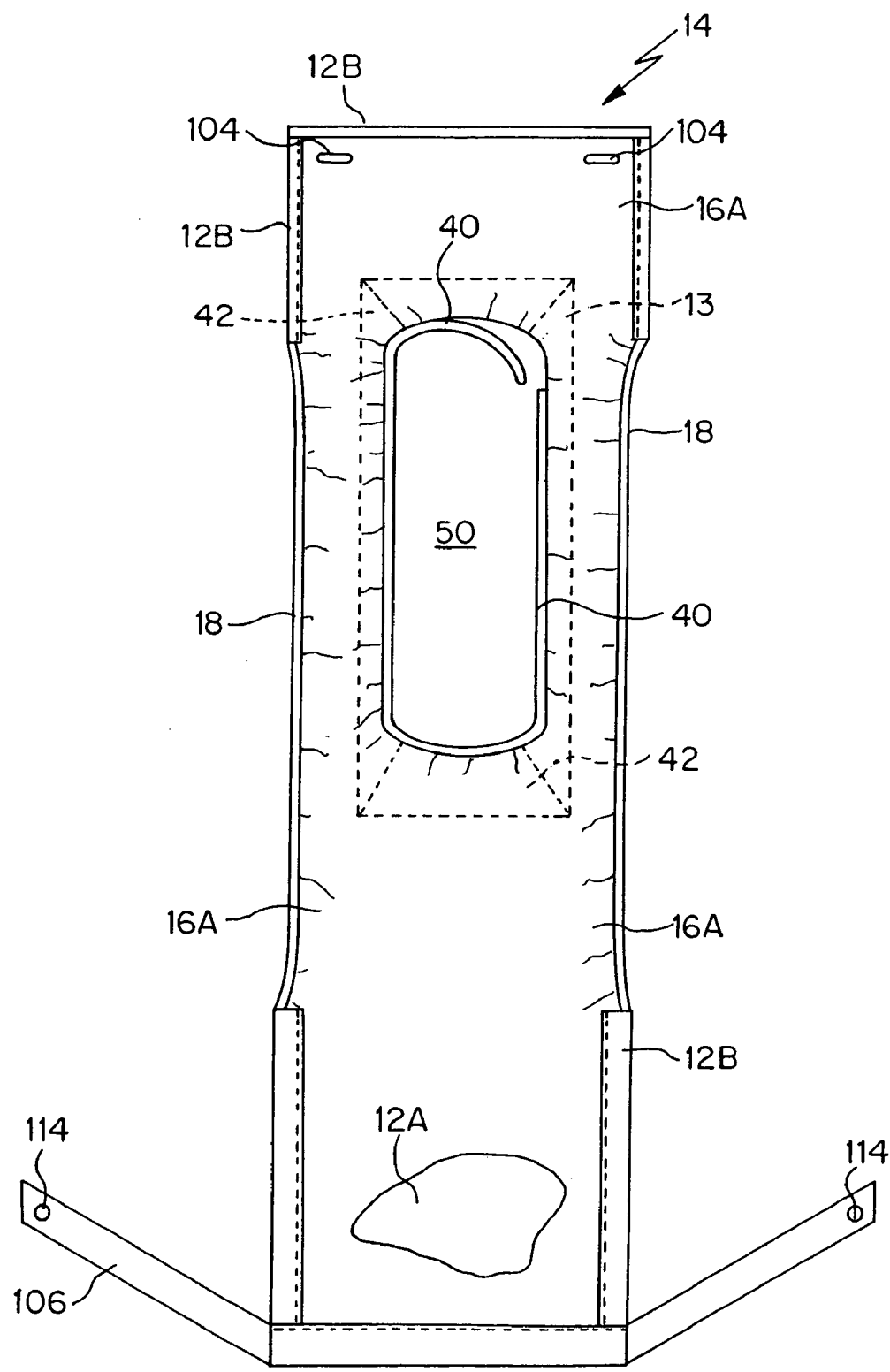
FIG. 9 is plan view of a belted undergarment with submerged pocket, produced per this invention, with partial cutaway to expose underlying shell.

In FIG. 9, the submerged pocket of FIGS. 7 and 8 is the same except, as shown, as a belted undergarment 14, where all principles of the invention are applied, and for fastening to the wearer, belt 106 with button 114 is coupled with buttonhole 104. Buttonhole 104 pierces with stitching both shell 12A and anchor cloth 16A. Folded edge 12B finishes the part of the undergarment.

Figure 10:
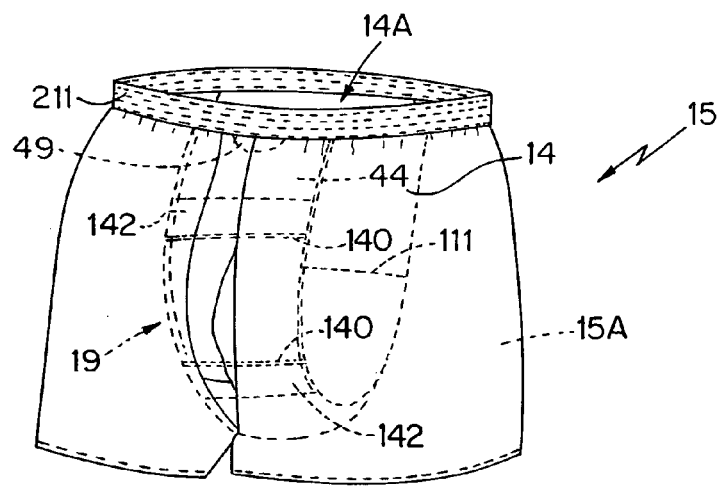
FIG. 10 shows another view of a man's boxer short with a pocketing sling anchored at the waistline.

In FIG. 10, like FIG. 5 there is a suspended pocketed sling, but in this boxer style garment the pocketed sling of FIG. 5 has been adapted to fit the male anatomy. For this boxer short garment, male boxer short garment 15 appears as a traditional boxer pant undergarment with waistline stitched with elastic 211 to hold the pant to the body of the wearer. Pocketed sling 19 is sewn under or to elastic 211 in the center back of short 15 at 14A. Pocketed sling frontal portion is centered at 49 and attached to or under elastic 211.

Figure 10A:
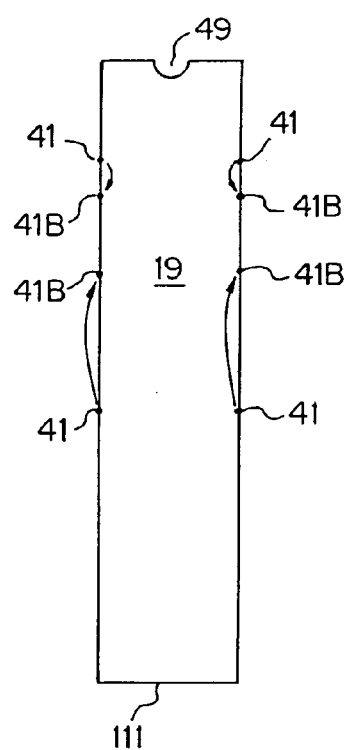
FIG. 10A shows the first step in creating the pocketed sling structure with parallel folds.

FIG. 10A shows the first step in creating the boxer version of the pocketed sling device. Crease line 41 (like crease line 410 of FIG. 5) now becomes the crease line for both a frontal and rear pocket of the pocketed sling structure. As in FIG. 5, crease line 41 is folded inward to notch 41B creating a three-ply thickness. The folds at the frontal and read ends may be identical to each other in depth, or as depicted different in depth.

Figure 10B:
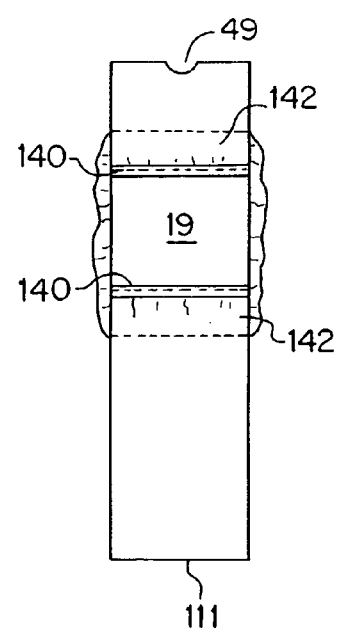
FIG. 10B shows the second step of manufacture, creating the pocketed sling with parallel elasticized folding regions.

In FIG. 10B, the pocket 142 is formed both in the frontal and rear portions of the garment. Crease line 41 is covered with elastic 140.

Figure 10C:
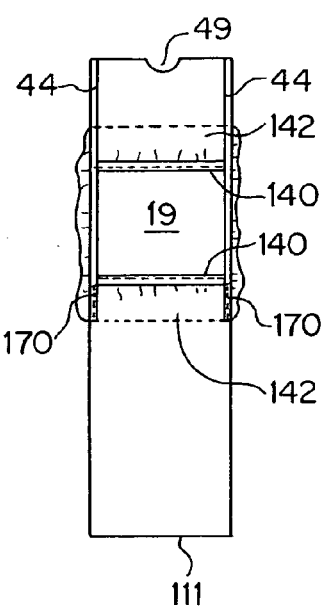
FIG. 10C shows the third manufacturing step in creating the pocketed sling with parallel elasticized folding regions and their parallel, vertical, elasticized sides.

In FIG. 10C, opposite side walls of pocketed-sling 19 receive elastic 44, as shown, to recess and cup the entire frontal portion of the sling to better fit to the male anatomy. Stitching at 170 holds the 3 plies of the S-folded fabric construction together at bottom pocket 142. Elastic 44 also serves the purpose of holding and stabilizing the 3 plies of the S-folded fabric pocket 142 construction together at the top fold of the pocket.

Figure 10D:
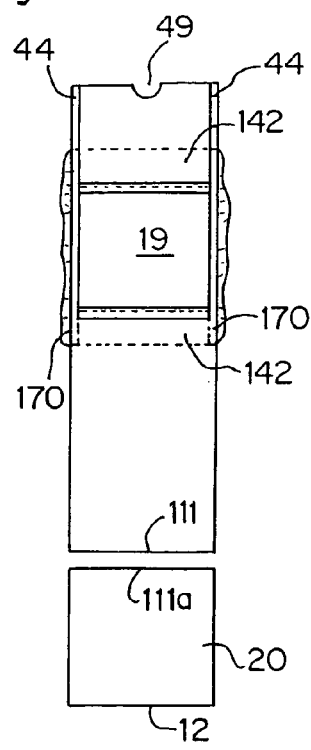
FIG. 10D depicts the pocketed sling formed and ready for attachment to an adjustable knit connecting piece.

FIG. 10D is a view of pocketed sling 19 where connecting seam edge 111A is to be joined to seam edge 111 of the terminal rear end of the pocketed sling 19 of waterproof or non-waterproof material. Piece 20 is ideally of stretch material and as a connecting piece to the boxer short that will be made to be of greater length for larger boxer shorts. Hence, the same pocketed sling device can be accommodated in many different sizes of boxer short simply by extending piece 20.

Figure 10E:
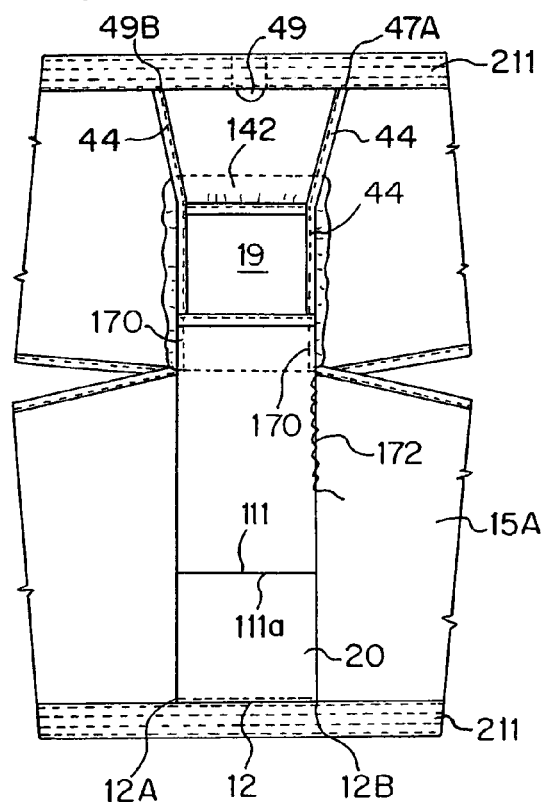
FIG. 10E shows the pocketed sling formed with its connecting knit fabric back and anchored to the frontal center portion of the boxer short, and anchored with stitching to the rear portion of the boxer short between the boxer fabric and the elastic waistband, retrofitted into the boxer short with anchor stitching in frontal and rear portions of the garment.

In FIG. 10E, the pocket sling 19 is attached at 111 and 111*a*, and then attached centrally to boxer outer shell 15 at notches 49B and 47A in the frontal interior waistband 211 and in the center rear attachment points, or notches, 12A, 12 and 12B. Alternatively, in FIG. 10F, fabric 14 is laid over the top of the waterproof material of pocketed sling 19, stitched at 47, the terminal end of fabric 14 being arcuate at 17 to waterproof the buttocks region of the garment while providing absorbent stretch material on top. Stitching 47 functions also to stabilize 3 plies of folded fabric, at opposite sides of pocket 142 in the same way stitching 170 stabilizes pocket 19 of FIGS. 10D and 10E. The extended piece of material with no waterproof material under it is identified by 14. Extended fabric 14, like separate piece of material 20 of FIG. 10D, may be adjusted in length to accommodate different sizes of boxer short outer material 15. This construction also offers an optional finishing overlock stitch 172 to the sidewalls of sling 19 in the rear portion of the garment.

Figure 10F:
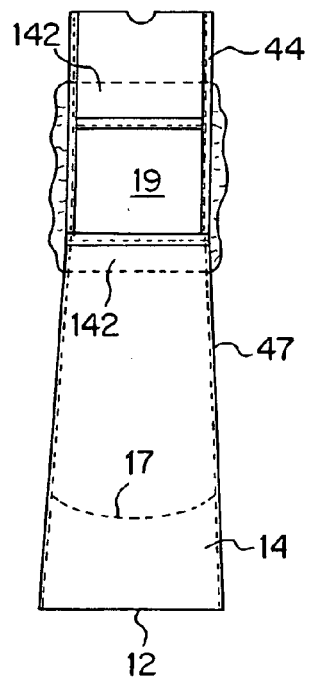
FIGS. 10F and 10G depict final steps in the construction of the pocketed sling short.
Figure 10G:
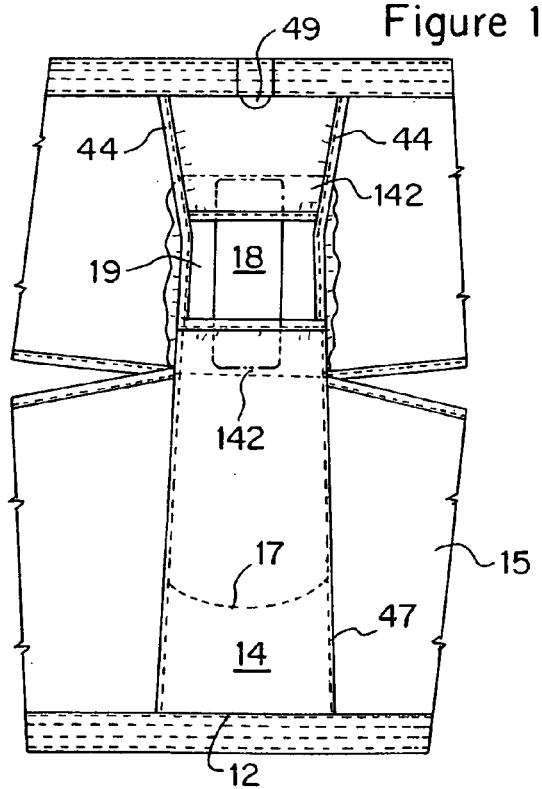

In FIG. 10G, the pocketed sling device of FIG. 10F is now attached to the interior portion 15A of garment 15 in the same manner as described with respect to FIG. 10E.

Figure 11:
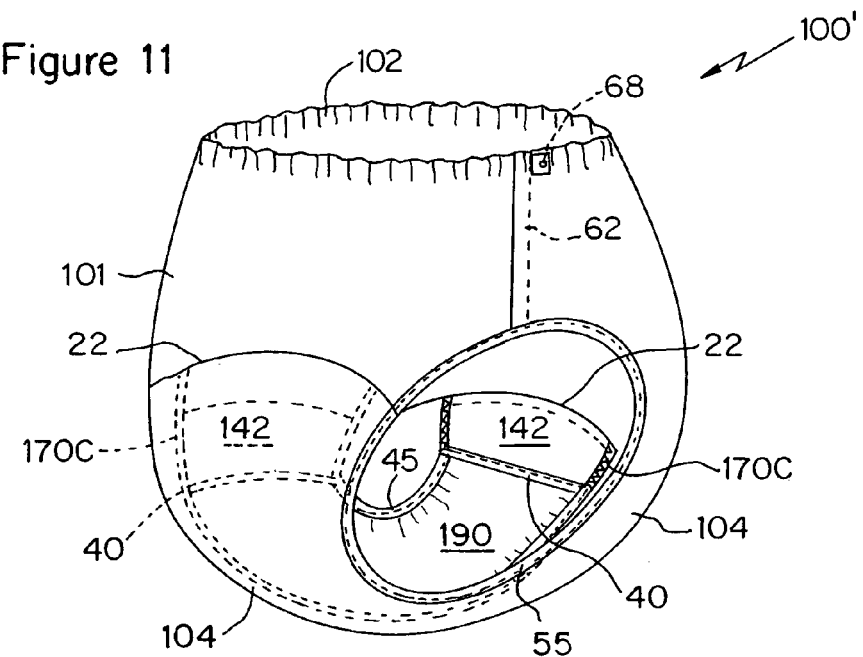
FIG. 11 depicts a garment implementing a pocketed sling, in accord with an embodiment helpful to wheel-chair bound or otherwise incapacitated users.
Figure 11A:
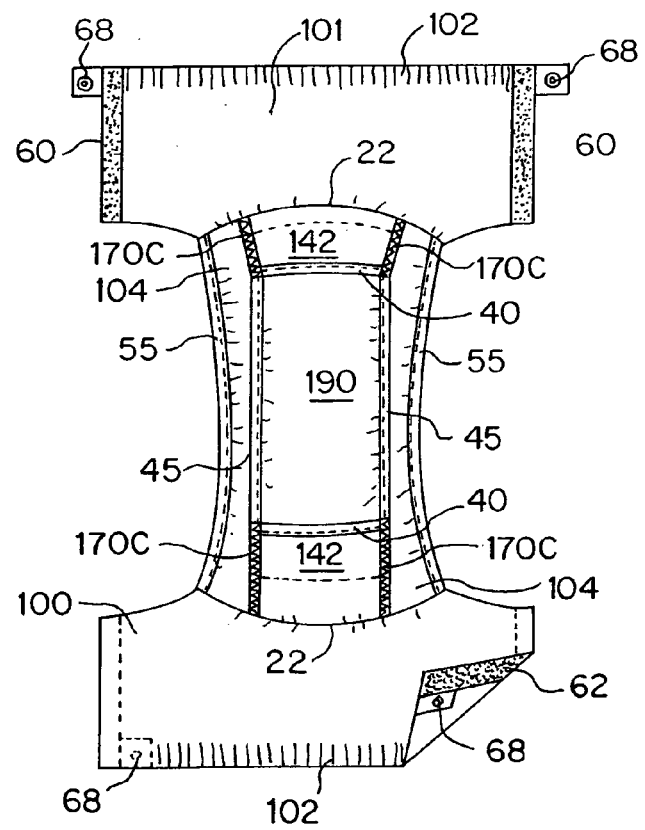
FIGS. 11A–E show manufacturing steps therefor.

In FIGS. 11 and 11A, the pocketed sling of FIGS. 5 and 10 has been adapted for wheel chair bound persons who cannot step into underwear but must be lifted or rolled onto or into underwear. Protective underwear garment 100' provides fastening at the tops using a combination of snaps 68 and Velcro® strip 60 of hook-type filamentary material and strip 62 of loop-type filamentary material to join together the sides of the garment 100' after the user of the garment is placed on top of the pant. Material 101 is preferably a stretch material with waist line 102 being of greater stretch material and joining line 22 being an arcuate joining line of material in the groin area of either waterproof or non-waterproof material 104. Elastic 55 is the leghole elastic of the groin region material 104, and suspended from the terminal ends of material 104 is the pocketed sling device 190 of construction similar to pocketed sling structure 19 of the boxer short except for omission of elastic 44 of the boxer short of FIG. 10. Elastic 44 has now been replaced by overlock stitching 170C. However, like FIG. 5 and FIG. 10, a three-ply folded pocket 142 is seen with its crease edge covered with elastic 40. The first ply portion is now covered with elastic at 45 but stops where the three-ply folds of material join at parallel stitching 170C at both the frontal and rear portions of the garment.

Figure 11B:
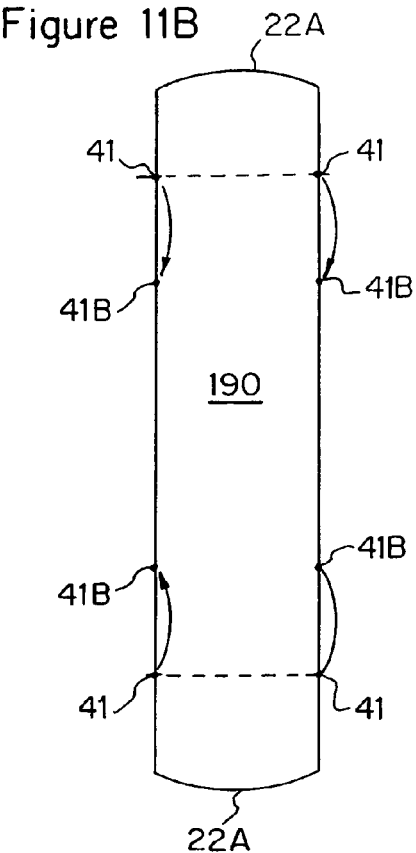
Figure 11C:
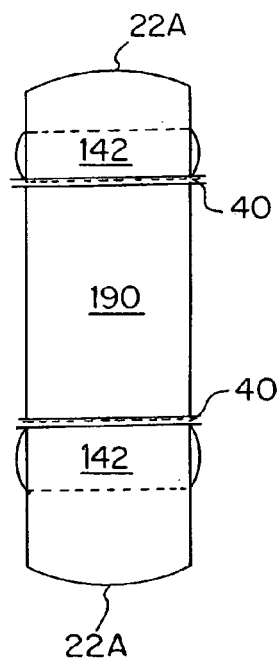
Figure 11D:
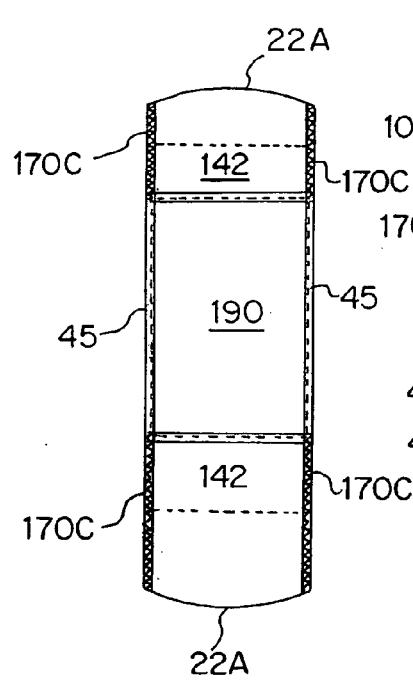

FIG. 11B depicts a first step in forming pocketed sling 190 where crease line 41 is folded to notch 41B on opposite sides and opposite ends forming, in FIG. 11C, three-ply material pockets, with crease line 41 covered by elastic 40. In FIG. 11D, this single ply of fabric portion is covered by elastic 45, and at the point where the two-ply fold joins the single ply material at an overlock stitch 170 finishes the edge and holds the three-ply material in place. The base of pocket 142 or terminal end of the folded portion of pocket 142 has no stitching and hence prevents migration of fluid out of the pocket.

Figure 11E:
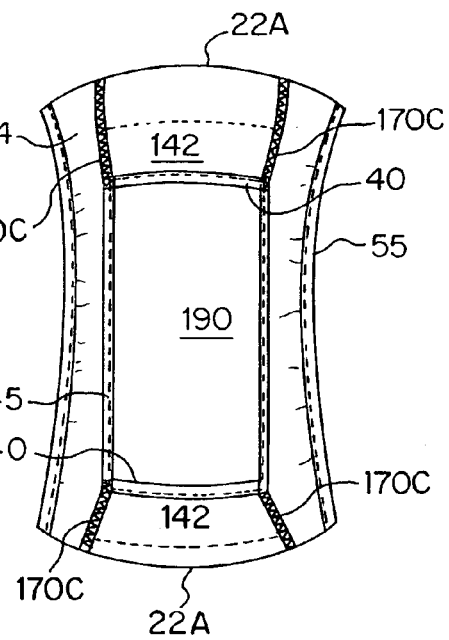

In FIG. 11E, pocketed sling 190 is joined at arcuate edge 22A, sealing material 104 and pocketed sling 190 together. Returning to FIGS. 11 and 11A, material edge 22A is now joined in seam line 22 to hold the entire protective pant together, i.e., stretch top material 101 to waterproof material 104 and the pocketed sling receptacle 190.

What is claimed is:

1. A protective undergarment, comprising:
   an outer layer of material shaped to conform to buttocks and leg regions of a user; and
   an elongated sling of material connected to the outer layer, wherein opposite sides of the sling are bowed inward and joined together at a first end of the sling to form a first pocket part for retaining one end of a fluid absorbent pad, a cuff being connected between the first end of the sling and the outer layer, a second end of the sling being connected to the outer layer, and an intermediate portion of the sling between the first and second ends of the sling being folded longitudinally into an S-shape so as to provide three plies of the material establishing a second pocket part for retaining an opposite end of the fluid absorbent pad,
   wherein at least one of the outer layer and elongated sling is made of a fluid resistant material.

2. The protective undergarment as in claim 1, wherein a first turn of material of the S-shaped intermediate portion of the sling is adapted to hold the opposite end of the pad, and a second turn of material is covered with elastic to bow and form-fit the second pocket part to the pad when the opposite end of the pad is held therein.

3. The protective undergarment as in claim 1, wherein sides of the sling are displaced inwardly from leg regions of the outer layer.

4. The protective undergarment as in claim 1, wherein the outer layer is of fluid-resistant material.

5. The protective undergarment as in claim 1, wherein the first and second ends of the sling are positioned at frontal and rear regions of the outer layer, respectively.

* * * * *